United States Patent
Ceron et al.

(10) Patent No.: US 6,181,973 B1
(45) Date of Patent: Jan. 30, 2001

(54) ANCHORING STRUCTURE FOR IMPLANTABLE ELECTRODES

(76) Inventors: Claudio Ceron, Strada Villanova 9, 1-10090 Castagneto Po (Torino); Guido Gaggini, Piazzale Martesana 6, 1-20128 Milano; Marco Vacchelli, Via San Giorgio 11, 1-10014 Caluso (Torino), all of (IT)

( * ) Notice: Under 35 U.S.C. 154(b), the term of this patent shall be extended for 0 days.

(21) Appl. No.: 09/348,963

(22) Filed: Jul. 7, 1999

(30) Foreign Application Priority Data

Apr. 2, 1999 (EP) .................................................. 99830190

(51) Int. Cl.$^7$ .................................................. A61N 1/362

(52) U.S. Cl. .......................................................... 607/126

(58) Field of Search .................................. 607/126, 122, 607/128

(56) References Cited

U.S. PATENT DOCUMENTS

| | | |
|---|---|---|
| 3,902,501 | 9/1975 | Citron et al. . |
| 3,943,936 | 3/1976 | Rasor et al. . |
| 3,971,364 | 7/1976 | Fletcher et al. . |
| 4,156,429 | 5/1979 | Amundson . |
| 4,236,529 | 12/1980 | Little . |
| 4,258,724 | 3/1981 | Balat et al. . |
| 4,269,198 | 5/1981 | Stokes . |
| 4,289,144 | 9/1981 | Gilman . |
| 4,301,815 | 11/1981 | Doring . |
| 4,332,259 | 6/1982 | McCorkle, Jr. . |
| 4,360,031 | 11/1982 | White . |
| 4,393,883 | 7/1983 | Smyth et al. . |
| 4,402,328 | 9/1983 | Doring . |
| 4,402,329 | 9/1983 | Williams . |
| 4,409,994 | 10/1983 | Doring . |
| 4,432,377 | 2/1984 | Dickhudt . |
| 4,437,475 | 3/1984 | White . |
| 4,443,289 | 4/1984 | Kölges et al. . |
| 4,444,206 | 4/1984 | Gold . |
| 4,454,888 | 6/1984 | Gold . |
| 4,458,677 | 7/1984 | McCorkle, Jr. . |
| 4,467,817 | 8/1984 | Harris . |
| 4,479,500 | 10/1984 | Smits . |
| 4,488,561 | 12/1984 | Doring . |
| 4,497,326 | 2/1985 | Curry . |
| 4,506,679 | 3/1985 | Mann . |
| 4,582,069 | 4/1986 | McArthur . |
| 4,585,013 | 4/1986 | Harris . |
| 4,590,950 | 5/1986 | Iwaszkiewicz et al. . |
| 4,643,201 | 2/1987 | Stokes . |
| 4,662,382 | 5/1987 | Sluetz et al. . |
| 4,716,888 | 1/1988 | Wesner . |
| 4,721,118 | 1/1988 | Harris . |
| 4,722,353 | 2/1988 | Sluetz . |
| 4,784,161 | 11/1988 | Skalsky et al. . |
| 4,796,643 | 1/1989 | Nakazawa et al. . |
| 4,841,971 | 6/1989 | Hess . |
| 4,913,164 | 4/1990 | Greene et al. . |

(List continued on next page.)

FOREIGN PATENT DOCUMENTS

| | | |
|---|---|---|
| 2 067 411 | 7/1981 | (GB) . |
| WO 98/20933 | 5/1998 | (WO) . |

OTHER PUBLICATIONS

European Search Report on European Patent Application No. EP 99 83 0190, including Annex, dated Dec. 13, 1999, 3 pages.

*Primary Examiner*—Scott M. Getzow

(57) ABSTRACT

In one embodiment, the structure comprises, in addition to a body which is usually cylindrical or tubular, a plurality of tines which extend radially from the body. The tines, which are usually flat in shape and tapered, are positioned, relative to the body, with a keying angle other than zero and hence in a generally helical arrangement. The principal axes of the tines in question are preferably also inclined to the longitudinal axis of the body, giving rise to a generally anchor-like shape.

21 Claims, 2 Drawing Sheets

U.S. PATENT DOCUMENTS

| | | |
|---|---|---|
| 4,917,106 | 4/1990 | Olivier . |
| 4,945,922 | 8/1990 | van Krieken . |
| 4,988,347 | 1/1991 | Goode et al. . |
| 5,016,646 | 5/1991 | Gotthardt et al. . |
| 5,044,375 | 9/1991 | Bach, Jr. et al. . |
| 5,074,313 | 12/1991 | Dahl et al. . |
| 5,090,422 | 2/1991 | Dahl et al. . |
| 5,179,962 | 1/1993 | Dutcher et al. . |
| 5,231,996 | 8/1993 | Bardy et al. . |
| 5,238,007 | 8/1993 | Giele et al. . |
| 5,257,634 | 11/1993 | Kroll . |
| 5,261,418 | 11/1993 | Ferek-Petric . |
| 5,300,107 | 4/1994 | Stokes et al. . |
| 5,303,740 | 4/1994 | Junier . |
| 5,324,327 | 6/1994 | Cohen . |
| 5,336,253 | 8/1994 | Gordon et al. . |
| 5,405,374 | 4/1995 | Stein . |
| 5,423,881 | 6/1995 | Breyen et al. . |
| 5,425,756 | 6/1995 | Heil, Jr et al. . |
| 5,439,485 | 8/1995 | Mar et al. . |
| 5,476,499 | 12/1995 | Hieschberg . |
| 5,476,500 | 12/1995 | Fain et al. . |
| 5,476,502 | 12/1995 | Rubin . |
| 5,545,206 | 8/1996 | Carson . |
| 5,562,723 | 10/1996 | Rugland et al. . |
| 5,571,157 | 11/1996 | McConnell . |
| 5,578,068 | 11/1996 | Laske et al. . |
| 5,645,580 | 7/1997 | Moaddeb et al. . |
| 5,683,447 | 11/1997 | Bush et al. . |
| 5,713,945 | 2/1998 | Fischer et al. . |
| 5,738,220 | 4/1998 | Geszler . |

ANCHORING STRUCTURE FOR IMPLANTABLE ELECTRODES

FIELD OF THE INVENTION

The present invention relates to structures for anchoring implantable electrodes. An implantable electrode is any device which can cooperate, in an electrically conductive relationship, with human or animal tissue in which it has been implanted. The invention has been developed with particular attention to its possible application to heart-stimulation electro-catheters with passive fixing.

BACKGROUND OF THE INVENTION

Structures related to the present invention are described in WO 98/20933 and the following U.S. Pat. Nos. 5,300,107; 4,796,643; 5,179,962; 4,402,329; 4,432,377; 4,269,198; 4,479,500; 4,945,922; 4,716,888; 4,437,475; 4,917,106; 5,336,253; 5,303,740; 5,074,313; 5,090,422; 5,423,881; 4,721,118; 4,662,382; 4,585,013; 4,582,069; 4,506,679; 4,497,326; 4,467,817; 4,301,815; 4,444,206; 4,409,994; 4,258,724; 3,943,936; 3,971,364; 3,902,501; 5,439,485; 4,488,561; 4,360,031; 4,443,289; 4,988,347; 4,454,888; 4,643,201; 5,016,646; 5,044,375; 5,231,996; 5,405,374; 4,393,883; 4,332,259; 4,402,328; 4,156,429; 4,590,950; 4,458,677; 4,236,529; 4,913,164; 4,841,971; 4,722,353; 4,289,144; 5,476,499; 5,476,500; 5,476,502; 5,425,756; 5,324,327; 5,261,418; 5,257,634; 5,238,007; 5,738,220; 5,713,945; 5,683,447; 5,578,068; 5,571,157;5,545,206; 5,562,723; 5,423,881; and 5,645,580. The contents of each of these U.S. patents is hereby incorporated by reference into this application.

Practically all of the solutions described in the documents cited above provide for the anchoring structure to be produced in the form of a body from which one or more projecting anchoring elements usually called "barbs" (or "tines" in current terminology) extend in a configuration generally comparable to that of an anchor. With a certain degree of simplification, but without departing very much from reality, the configurations of the tines in the above-mentioned documents can be divided substantially into two basic types: (1) the type which provides for the tines to be produced in the form of small bars which are generally cylindrical throughout their length between the proximal region connected to the body of the structure and the distal end (see, for example, U.S. Pat. No. 4,269,198); and (2) the type in which the tines have a generally flattened configuration, possibly with dimensions which decrease gradually from the proximal region (of substantially elongate shape) connected to the body of the structure, towards the distal end. An example of this second type of configuration is described in U.S. Pat. No. 4,945,922. This configuration provides for the use of tines of flattened shape which have a slightly arcuate profile in a generally semi-cylindrical configuration so that the tines can fit better against the wall, which is usually cylindrical, of the body of the anchoring structure when they are folded to the position for the insertion of the electrode towards the implantation site.

In the configuration described in U.S. Pat. No. 4,945,922, the proximal regions of the tines extend along a path substantially aligned with the direction of the planes transverse the principal axis of the body of the anchoring structure. In contrast, in the configurations described in U.S. Pat. Nos. 4,721,118, 4,585,013, and 4,467,817, this proximal region extends along a path substantially aligned with one of the generatrices of the cylindrical body of the structure and hence in a direction parallel to the principal longitudinal axis of the body. This configuration (see, for example, FIG. 4 of U.S. Pat. No. 4,721,118) enables the tines to be brought to a position in which they are wrapped around and close to the body of the anchoring structure when it is confined inside a sheath used for positioning it at the implantation site by catheterization. To adopt the terminology which is conventional in the field of the propellers (helices) to which reference will be made below, the configuration described in U.S. Pat. No. 4,945,922 may be seen as a configuration in which the tines of flattened profile have a keying angle of 0°. On the other hand, in the configuration described in U.S. Pat. No. 4,721,118, the tines in question have a keying angle of 90°.

Tines of the types referred to above have some intrinsic disadvantages, even when they are used in combination. For example, tines with a bar-like, typically circular profile tend to be too inflexible in the proximal region connected to the body of the anchoring structure. Moreover, when they are folded close to the body of the anchoring structure in the insertion position, these tines tend to project quite significantly relative to the outline of the body of the restraining structure.

Flattened tines with "zero" keying angles can be made to fit quite closely against the body of the restraining structure at the insertion stage. However, their small cross-section in the proximal region means that the tines often have inadequate behavior during the resilient opening-out stage after positioning at the implantation site. Moreover, the low resistance of the proximal region to bending exposes the tines to the risk that even a slight stress applied to the electrode in the direction away from the implantation site causes the tines to turn over from the generally anchor or arrow-like (harpoon-like) configuration which can ensure firm anchorage of the electrode at the implantation site.

Tines with "90°" keying angles have the undoubted advantage of rendering independent the flexural characteristics of the proximal regions of the tines which come into play, respectively, when the tines are wrapped around the body of the anchoring structure, and when they are unfolded from the body in question, projecting radially like fins relative to the anchoring structure. In the first situation, the proximal regions of the tines are in fact subjected to bending stress relative to their smallest dimension, thus showing a high degree of flexibility. In the second situation, the bending stress acts in the direction in which the extent of the proximal regions of the tines is greatest so that they show much greater strength and stiffness.

However, even this latter solution is not free of problems. It in fact imposes limitations due to the number and radial extent of the tines which can be arranged on the body of the anchoring structure in the same region of its axial extent. This is because it is necessary to prevent the tines from coming close together and interfering with one another while they are being wrapped around and close to the body of the anchoring structure. This is disadvantageous both because of a possible increase in the radial dimensions of the unit due to the superimposition of the tines, and because of possible problems of interference during the unfolding stage. In this connection, it should be noted that the unit formed by the tines and by the body of the anchoring structure is usually a one-piece elastomeric component which has the appearance of a bush from which the tines extend.

There is, moreover, a tendency to reject solutions which provide for the use of tines which are offset relative to one another along the axis of the body of the anchoring structure, since it is usually preferred to be able to fit at least four tines uniformly distributed angularly on the same axial portion of the body.

The object of the present invention is to provide an anchoring structure of the type specified above in which the above-mentioned problems are finally overcome. According to the present invention, this object is achieved by means of an anchoring structure having the specific characteristics described in this specification and recited in the claims.

SUMMARY OF THE INVENTION

In particular, the solution according to the invention provides tines which are particularly thin but also stiff to ensure anchorage of the electrode. During insertion, the tine is bent along its natural bending plane by a twisting movement on the body of the anchoring structure, the slight thickness of the tine enabling it faithfully to reproduce the profile of the body. During use, however, a high degree of stiffness with respect to forces directed along the longitudinal axis of the structure is ensured since this is a direction other than the natural direction of bending of the tine. These forces are those which are exchanged between the tines and the heart trabeculae so that, in the solution according to the invention, the tines ensure more effective anchoring than any tine of equal size, for example, of the triangular type with a "zero" keying angle. Again in comparison with known structures of this type, the solution according to the invention enables the width of the tine to be increased, for given frontal dimensions. This helps further to stiffen the tine, for a given overall size.

Moreover, during implantation, the tines can be fitted in the insertion device (which is usually constituted by a tubular body) by first engaging the farthest forward portion of the proximal region of each tine, and then proceeding along the remainder of the bodies of the tines. This ensures, for the doctor performing the implantation, a smoother feel of the catheter of which the anchoring structure constitutes the head portion inside the insertion device.

According to an embodiment of the invention which has been found particularly advantageous, a keying angle of about 30° is selected, the tines also having a substantially triangular, tapered shape with an angle of about 14° at the tip of the triangular profile. With regard to the general angle of inclination of the tines (defined as the angle formed between the principal longitudinal axis of the tine and the longitudinal axis of the body of the supporting structure, this latter axis in practice identifying the direction of advance of the anchoring structure during implantation), the selection of a value in the region of about 45° has been found particularly advantageous.

BRIEF DESCRIPTION OF THE DRAWINGS

The invention will now be described, purely by way of non-limiting example with reference to the appended drawings.

DETAILED DESCRIPTION OF THE PREFERRED EMBODIMENTS

Figure 1:
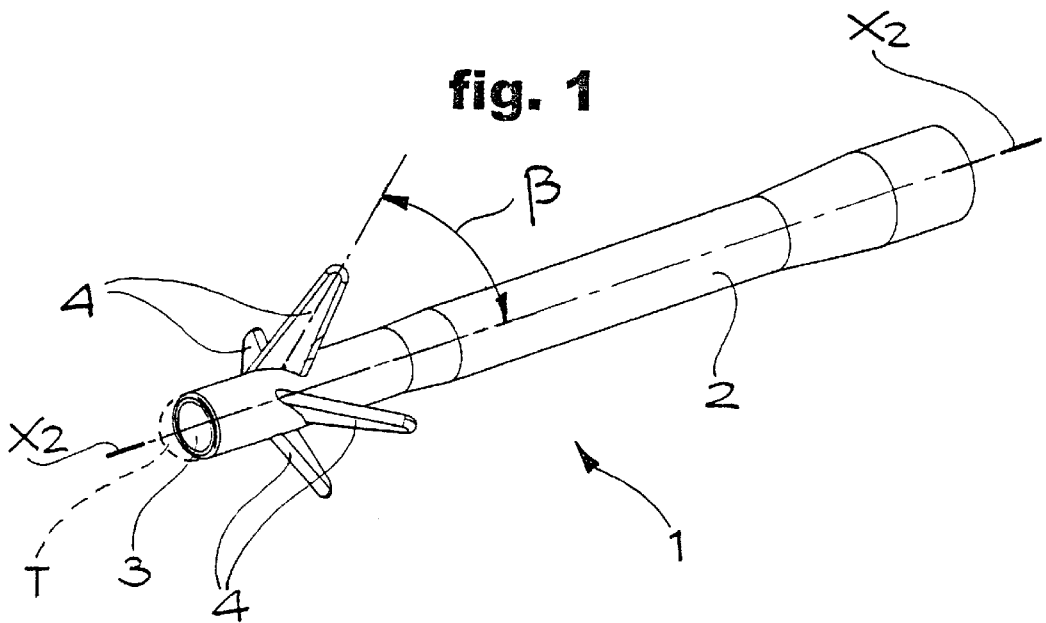
FIG. 1 is a general perspective view of an anchoring structure according to the invention.

In the drawings, an anchoring structure for implantable electrodes is generally indicated 1. For the meaning of the term "implantable electrode", reference should be made to the introductory portion of the present description. Also refer to the introductory portion for a description of the general criteria for the production and use of the structure 1.

As already indicated above, the invention relates primarily to the tines of the structure 1. As for the rest, the characteristics of the similar structures described in the documents mentioned in the introductory portion of the present description may therefore be reproduced, in general, for the structure 1. It will suffice herein to note that the structure 1 is constituted in general (including the tines) by a single shaped body of generally flexible material compatible with the requirement to be implanted in a human or animal body. For example, this may be a silicone elastomer material.

The structure 1 is usually composed of a generally tubular body 2. This shape enables the electrode, which is not shown since it is of known type, to pass through and/or to be positioned in the body 2. A tip T of the electrode (shown in broken outline in FIGS. 1 and 2) is in fact intended to project beyond the distal end 3 of the body 2, which extends along a principal axis indicated X2. A plurality of tines, generally indicated 4, extend from the body 2 (usually in the vicinity of the distal end 3) in a geometrical arrangement which, for the reasons explained further below, can be defined both as anchor-like and as propeller-like (helix-like).

Figure 4:
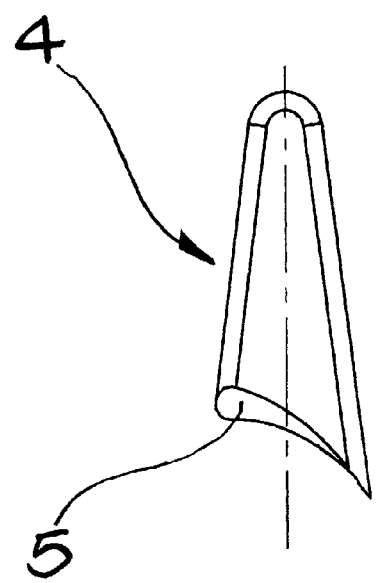
FIG. 4 shows, in greater detail, the geometrical characteristics of the barbs (tines) associated with the structure in question.

Thus, as can best be seen in the detailed view of FIG. 4 (in which one of the tines 4 is shown individually), each of the tines 4 preferably has a smooth and flattened shape with an approximately rectangular profile with rounded side and end edges. Moreover, it should be noted that, in the currently preferred embodiment of the invention, the tines 4 are formed integrally with the body 2 of the structure 1. The projecting portion of the structure of each tine 4 preferably has an isosceles triangular profile with an apex angle of the order of about 14°.

Figure 2:
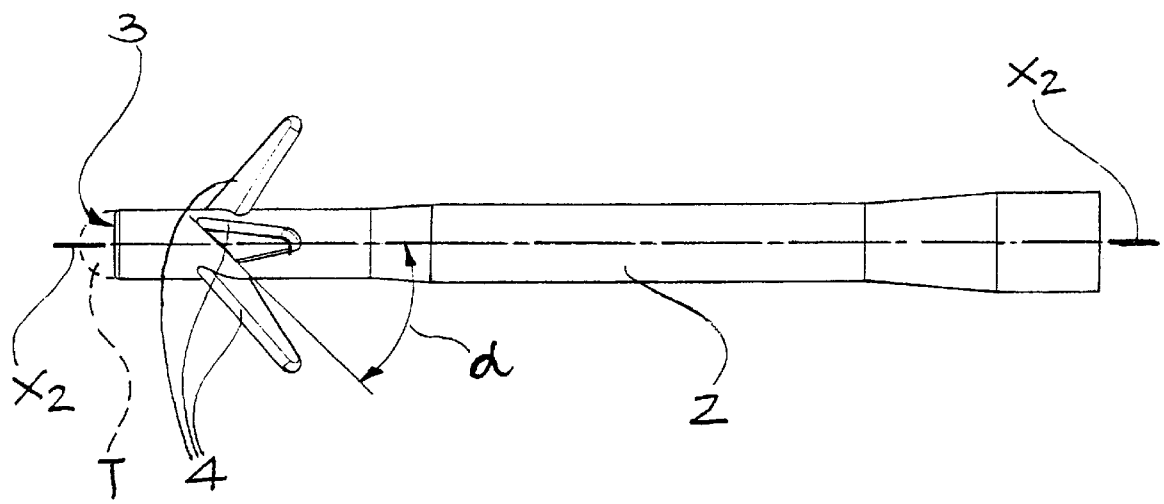
FIG. 2 is a side elevational view of the same structure.
Figure 3:
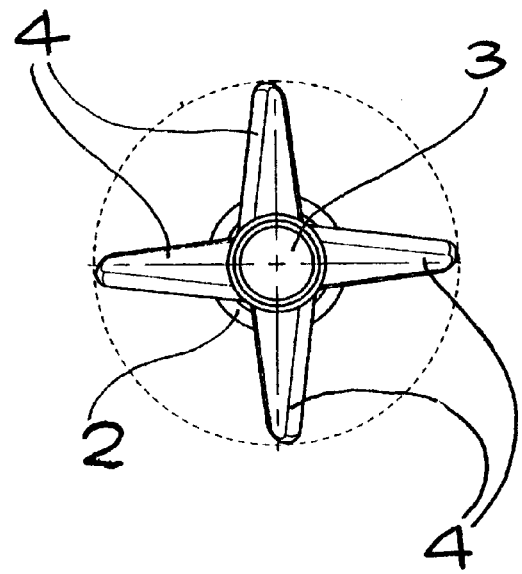
FIG. 3 is a front view of the structure of FIGS. 1 and 2.

An observation of FIGS. 1 and 2 in combination shows that, in contrast with the tines with "zero" and "90°" keying referred to in the introductory portion of this description, the tines 4 according to the invention are formed so as to have a keying angle ($\alpha$) typically of about 30°. This is why they are likened above to a propeller structure. In more strictly geometrical terms, the arrangement of the tines 4 according to the invention may be described with reference to the proximal regions 5 of the tines 4 (see FIG. 4) which have a generally elongate shape extending along a helical path. This path is centered about the principal axis X2 of the structure 2 and has an angle of twist corresponding to the above-mentioned keying angle (preferably about 30°).

Another possible way of describing the geometry of the configuration in question (with reference, for example, to bodies 2 which do not necessarily have a cylindrical shape but, for example, have a prismatic shape) is to say that the aforementioned proximal regions 5 extend along generally slanting or oblique paths both relative to the direction defined by planes perpendicular to the longitudinal axis X2 and relative to the axis X2 itself (this being intended to indicate briefly that the aforesaid paths are slanting or oblique relative to any of the planes included within the family of planes passing through the axis X2). It will also be appreciated from an observation of FIGS. 1 and 2, particularly FIG. 2, that (according to a known solution) the principal axes of the tines 4 are also generally inclined relative to the axis X2. The respective angle of inclination ($\beta$) selected, indicated in FIG. 1, is preferably about 45°. This is why they are likened above to an anchor structure.

When compared with solutions with "zero" keying, in the first place, the solution according to the invention benefits from the high degree of flexibility of each tine 4 when it is folded (in practice wrapped) close to the body 2 by bending of its proximal region 5 transversely where it is thinnest, and hence in the direction in which it presents least resistance to bending and also takes up the least space once folded against the body 2. This is combined with the high degree of strength shown by the tines in the typical condition of use after unfolding with respect to stresses in the direction identified substantially by the longitudinal axis X2 of the structure 1 and hence acting on the proximal region 5 to a large extent "lengthwise".

In comparison with solutions with "90°" keying, the solution according to the invention has two basic advantages. In the first place, precisely because the tines 4 are not folded close to the body 4 in a completely circular arrangement but in a helical arrangement, it is possible (particularly with the use of tines 4 which are tapered gradually towards the distal end) to fit three, four, or possibly even more tines 4 on the same longitudinal portion of the body 2. This is achieved whilst preventing the tines in question from covering and interfering with one another whilst they are being folded close to the body 2. If other parameters remain the same, this permits the production of tines 4 of greater radial length if desired and, in particular, tines which, when folded close to the body 2, have a circumferential extent greater than the circumferential separation between the proximal regions 5 of adjacent tines 4. Naturally, the term "circumferential" relates to the body 2. The other advantage lies in the fact that, when fitted in the respective insertion device (which is usually constituted by a tubular sheath), the structure I does not oppose the insertion movement with tines 4 extending completely (particularly with regard to their proximal regions) along the axis X2 which is also the insertion axis. Rather, the fact that the proximal regions 5 are in a slanting or oblique arrangement relative to this axis means that the structure according to the invention is very compliant and easy to insert.

In particular, by adjusting parameters such as the number of tines 4 and their keying angle (it should be remembered that the solution described herein, which provides for the presence of four tines 4 with a keying angle of about 30°, is given purely by way of example) it is possible to produce anchoring structures 1 with characteristics which are differentiated according to specific requirements of use. For example, a reduction in the keying angle will produce, in general, a structure 1 which is more compliant upon being fitted in the insertion device but which at the same time is less resistant to stresses along the principal axis X2. An increase in the keying angle, on the other hand, will generally produce a structure which is less compliant upon being fitted in the insertion device but which is intrinsically more resistant to stresses at the implantation site.

It is stressed that the remarks just made also apply to the other parameters considered. Clearly, in fact, by adjusting these other parameters (the number and thickness of the tines 4, their geometrical arrangement, angle of inclination, etc.), as well as the keying angle, it is possible to achieve even greater flexibility in the definition of the functional parameters.

Naturally, the principle of the invention remaining the same, the details of construction and forms of embodiment may be varied widely with respect to those described and illustrated, without thereby departing from the scope of the invention as defined in the appended claims.

What is claimed is:

1. A structure for anchoring implantable electrodes comprising a body extending along a principal axis and at least one tine which can extend, relative to the body, from a proximal region of substantially elongate shape connected to the body and extending along a respective path, wherein the proximal region extends along a path which is slant both relative to the principal axis and relative to the direction of planes perpendicular to the principal axis.

2. A structure according to claim 1, wherein the path along which the proximal region extends is oriented, relative to the direction of planes perpendicular to the principal axis, at a keying angle of approximately 30°.

3. A structure according to claim 1, wherein the structure comprises a plurality of tines arranged in a generally helical distribution relative to the body.

4. A structure according to claim 2, wherein the structure comprises a plurality of tines arranged in a generally helical distribution relative to the body.

5. A structure according to claim 3, wherein the tines of the plurality are located on the same longitudinal portion of the body.

6. A structure according to claim 4, wherein the tines of the plurality are located on the same longitudinal portion of the body.

7. A structure according to claim 3, wherein the tines are generally tapered away from the proximal region.

8. A structure according to claim 4, wherein the tines are generally tapered away from the proximal region.

9. A structure according to claim 5, wherein the tines are generally tapered away from the proximal region.

10. A structure according to claim 6, wherein the tines are generally tapered away from the proximal region.

11. A structure according to claim 3, wherein when folded close to the body, each of the tines of the plurality has a circumferential extent greater than the circumferential separation between the proximal regions of adjacent tines.

12. A structure according to claim 5, wherein when folded close to the body, each of the tines of the plurality has a circumferential extent greater than the circumferential separation between the proximal regions of adjacent tines.

13. A structure according to claim 1, wherein the structure comprises four tines.

14. A structure according to claim 1, wherein the at least one tine has a substantially flat shape.

15. A structure according to claim 1, wherein the at least one tine has a substantially triangular profile.

16. A structure according to claim 15, wherein the substantially triangular profile has an apex angle of approximately 14°, opposite the proximal region.

17. A structure according to claim 1, wherein the at least one tine is arranged with its principal axis substantially inclined to the principal axis of the body.

18. A structure according to claim 17, wherein the at least one tine is arranged with its principal axis inclined to the principal axis of the body at an angle of approximately 45°.

19. A structure according to claim 1, wherein the at least one tine is formed integrally with the body.

20. A structure according to claim 1, wherein the structure is made of an elastomeric material.

21. A structure according to claim 20, wherein the elastomeric material is a silicone elastomer.

* * * * *